(12) United States Patent
Krafczyk et al.

(10) Patent No.: US 6,531,539 B2
(45) Date of Patent: Mar. 11, 2003

(54) ORGANOSILICON COMPOUNDS

(75) Inventors: Roland Krafczyk, Rheinfelden (DE); Rudolf Michel, Freigericht (DE); Jörg Münzenberg, Hanau (DE); Hans-Detlef Luginsland, Köln (DE)

(73) Assignee: Degussa AG, Dusseldorf (DE)

( * ) Notice: Subject to any disclaimer, the term of this patent is extended or adjusted under 35 U.S.C. 154(b) by 14 days.

(21) Appl. No.: 09/825,866

(22) Filed: Apr. 5, 2001

(65) Prior Publication Data

US 2001/0056139 A1 Dec. 27, 2001

(30) Foreign Application Priority Data

Apr. 8, 2000 (DE) .......................... 100 17 654

(51) Int. Cl.$^7$ ............... C08L 83/04; C07F 7/00; C07F 7/02; C07D 285/16
(52) U.S. Cl. ............... 524/588; 528/38; 528/40; 528/43; 556/407; 556/413; 556/427; 556/431; 544/3; 544/7
(58) Field of Search ............... 556/407, 413, 556/427, 431; 524/588; 544/3, 7; 528/38, 40, 43

(56) References Cited

U.S. PATENT DOCUMENTS

| 5,283,274 A | | 2/1994 | Seibert et al. | |
|---|---|---|---|---|
| 5,548,006 A | * | 8/1996 | Hirabayashi et al. | ....... 524/100 |
| 5,976,512 A | * | 11/1999 | Huber | .......................... 424/400 |
| 5,998,562 A | * | 12/1999 | Mahr et al. | .................... 528/21 |

FOREIGN PATENT DOCUMENTS

| DE | 21 47 581 | 3/1972 |
|---|---|---|
| DE | 44 24 582 | 1/1996 |
| DE | 199 02 484 | 7/1999 |
| EP | 0 065 477 | 11/1982 |
| EP | 0 845 493 | 6/1998 |
| EP | 1 074 582 | 2/2001 |
| JP | 62100462 A1 * | 5/1987 |
| JP | 04011684 A1 * | 1/1992 |

OTHER PUBLICATIONS

Goan et al., "Silicon–containing s–triazine derivatives", Journal of Organic Chemistry, Bd. 27, Jul. 1962, p. 2657–2658, XP001004345.
Hashim et al., "The effect of bis(3–triethoxysilylpropyl) tetrasulfide on silica reinforcement of styrene–butadiene rubber", Rubber Chemistry and Technology, Bd. 71, Nr. 2, May 1998, pp. 289–299, XP000767947.
Database WPI, Derwent Publications XP002169923 Apr. 1982.
English language abstract of DE 199 02 484 Jul. 1999.
English language abstract of DE 21 47 581 Mar. 1972.
English language abstract of DE 44 24 582 Jan. 1996.

\* cited by examiner

*Primary Examiner*—Robert Dawson
*Assistant Examiner*—Jeffrey B. Robertson
(74) *Attorney, Agent, or Firm*—Pillsbury Winthrop LLP

(57) ABSTRACT

The invention is directed to organosilicon compounds of the general formula

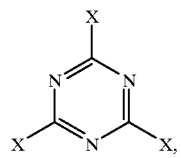

prepared by reacting triazine compounds with functional groups (e.g., chlorine) and corresponding compounds (e.g., mercapto). The organosilicon compounds can be used in rubber mixtures.

5 Claims, No Drawings

ORGANOSILICON COMPOUNDS

CROSS REFERENCE TO RELATED APPLICATIONS

The present application claims priority to German application 100 17 654.9 filed on Apr. 8, 2000, the subject matter of which is hereby incorporated by reference.

FIELD OF THE INVENTION

The present invention relates to organosilicon compounds, a process for their preparation and their use.

BACKGROUND OF THE INVENTION

It is known that sulfur-containing organosilicon compounds, such as 3-mercaptopropyltrimethoxysilane, 3-mercaptopropyltriethoxysilane, 3-thiocyanatopropyltriethoxysilane or bis-(3-triethoxysilylpropyl)tetrasulfane and -disulfane, are employed as silane adhesion promoters or reinforcing additives in rubber mixtures comprising oxidic fillers. The rubber mixtures are used, inter alia, for industrial rubber articles and for components of car tires, in particular for treads (DE 2 141 159, DE 2 212 239, U.S. Pat. No. 3,978,103, U.S. Pat. No. 4,048,206).

It is also known that the alkoxysilyl function, usually a trimethoxysilyl or triethoxysilyl group, reacts with the silanol groups of the filler, usually silica, during preparation of the mixture and the silane is thus fixed on the filler surface. The filler-rubber bond is then formed during the vulcanization process via the sulfur functionality of the fixed silane. So-called blocked mercaptosilanes have proven to be particularly effective for this use (WO99/09036). These compounds contain a polymer-reactive monosulfane function which is saturated with carbonyl-like groups. These carbonyl-like blocking groups can also be, in addition to groups such as —C(=O)R, —C(=S)R and —C(=NR')R, heterocarbonyls, such as sulfone groups, phosphone groups and others. The essential advantage of these compounds is that premature reaction of the polymer-reactive sulfur function can be suppressed by targeted activation of this function. The production reliability of rubber articles with a silica filler content is increased significantly by these products.

In addition, it is known from the literature that triazines are very active vulcanization accelerators. When these compounds are employed, nitrosamine formation can be suppressed, which represents an important toxicological and ecotoxicological advantage of these systems (H. Westlinning, Kautschuk, Gummi, Kunststoffe 23 (1970) 219; E. Morita, A. B. Sullivan, A. Y. Coran, Rubber Chem. Technol. 58 (1985) 284). Derivatives carrying amino groups and polysulfidic groups in particular are interesting alternatives to conventional accelerators, since in addition to their positive influence on the vulcanization, they also additionally act as sulfur donors (Ullmann's Encyclopedia of Industrial Chemistry, 4th edition, vol. A23, p. 375).

A disadvantage of the known organosilicon compounds is that they do not act simultaneously as good adhesion promoters and good vulcanization accelerators, sulfur donors, crosslinking agents or anti-ageing agents.

SUMMARY OF THE INVENTION

The object of the present invention is to provide triazine-functional adhesion promoters which, in addition to their function as adhesion promoters in the vulcanization products, simultaneously also act as vulcanization accelerators, sulfur donors, crosslinking agents or anti-ageing agents.

The invention provides an organosilicon compound of the general formula I

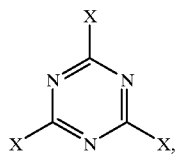

(I)

which is characterized in that the substituents X are identical or different and X is one of the following groups A, B or C:
A=Y—$R^1$—$S_n$—, where

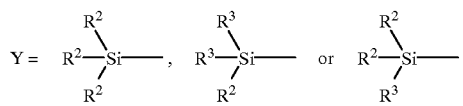

where
$R^2$=alkoxy radical having 1 to 4 C atoms,
$R^3$=alkyl radical having 1 to 8 C atoms,
$R^1$=linear or branched hydrocarbon having 1 to 10 C atoms,
n=1–8 or mixtures thereof,
B=$OR^4$, $NR^5R^6$, $SR^7$, SCN or —CO—$R^8$ where
$R^4$, $R^5$, $R^6$, $R^7$=H, branched or unbranched alkyl radical having 1–10 C atoms or substituted or unsubstituted aromatic radical having 6–30 C atoms, which is optionally interrupted by N, S or O atoms,
$R^8$=linear or branched alkyl radical having 1–20 C atoms, preferably methyl or long-chain uneven-numbered alkyl radicals $C_9$–$C_{17}$,
C=$(S_m)$/2 where
m=1–8 or mixtures thereof
with the proviso that the group C bridges two triazine units; at least one group A is present in the molecule; and the combination of a group A together with two mercapto groups or a mercapto group and an amino group $NR^5R^6$ is excluded.

Appropriately substituted triazine compounds can act as crosslinking agents between rubber chains and filler. In these cases at least one substituent can react with the filler and at least one substituent can react with the polymer.

Appropriate substituents can act as sulfur donors.

Appropriately substituted triazine compounds can act as crosslinking agents between various rubber chains. In these cases at least two substituents of the triazine molecule can react with different rubber chains and join the rubber chains via the rigid triazine unit.

With appropriately substituted triazine compounds, an anti-ageing agent bonded as a substituent on the triazine ring can be introduced into the rubber. Substances which can have such actions are, for example, aromatic amines and phenols (Ullmann's Encyclopedia of Industrial Chemistry, 4th edition, vol. 23, p. 383 et seq.).

It is known that the three Cl atoms in cyanuric chloride can be replaced selectively by nucleophiles (V. I. Mur, Russian Chem. Rev. 33 (1964) 92, Ullmann's Encyclopedia of Industrial Chem., 4th edition, vol. A8, p. 195 f).

The invention also provides a process for the preparation of organosilicon compounds of the formula I, which is characterized in that group A is obtained:

by reaction (II) of a chlorine-substituted triazine base skeleton with mercaptosilanes of the corresponding structure in the presence of an acid-trapping agent, for example tertiary amines, alkali metal carbonates or by blowing out the HCl gas formed, a mono- di- or trisubstitution being obtained selectively, depending on the number of chlorine atoms on the triazine skeleton and on the molar ratio of triazine:mercaptosilane, or (II)

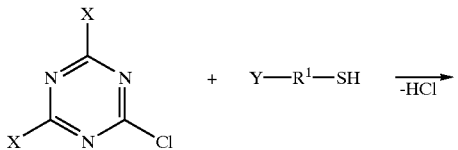

by reaction (III) of a metallized mercaptotriazine with a chloroalkylsilane corresponding to grouping A and, for n>1, in the presence of elemental sulfur, (III)

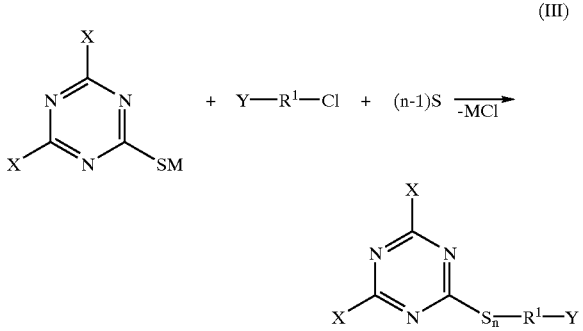

where M=H, metal, for example Na, K or Li;
group B is obtained:

by reaction (IV) of a chlorine-substituted triazine skeleton with corresponding alcohols, amines, and mercaptans in the presence of an acid-trapping agent, for example a tertiary amine (in the case of reaction with an amine in the presence of an excess of the same amine), alkali metal carbonates or by blowing out the HCl gas formed (IV)

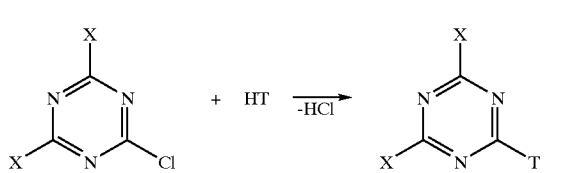

where T=$OR^4$, $NR^5R^6$ or $SR^7$, by reaction (V) of a chlorine-substituted triazine skeleton with corresponding metallized alcohols, amines, and mercaptans or (V)

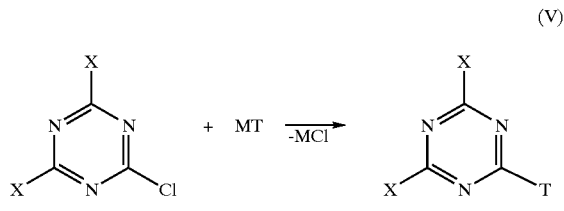

by alkylation (VI) of corresponding amino- and mercaptyl-substituted triazines with highly alkylating substances Z=I, Br, Cl, $(SO_4)_{0.5}$, $O_3S$—

(VIa)

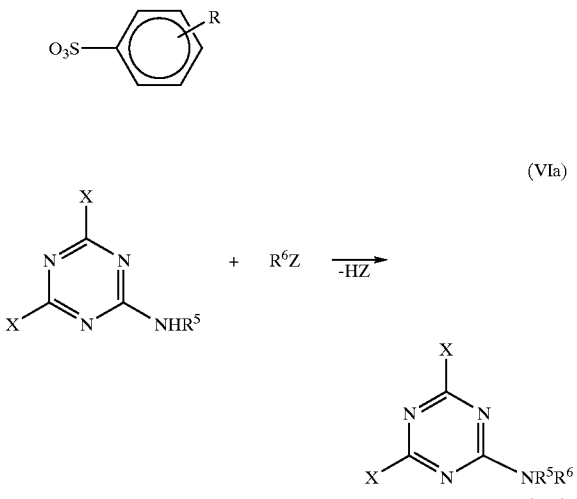

(VIb)

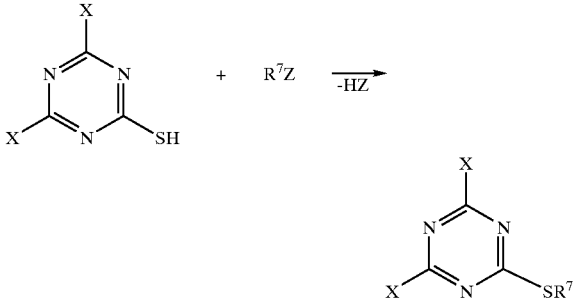

and group C is obtained by reaction of a chlorine-substituted triazine with a sodium polysulfide (VII)

(VII)

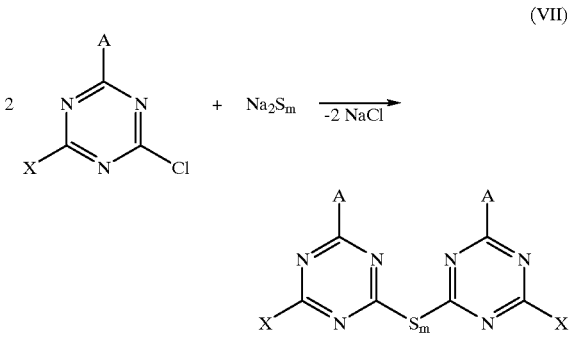

or a mixture of sodium sulfide (VIIIa) or sodium hydrogen sulfide (VIIIb) and sulfur

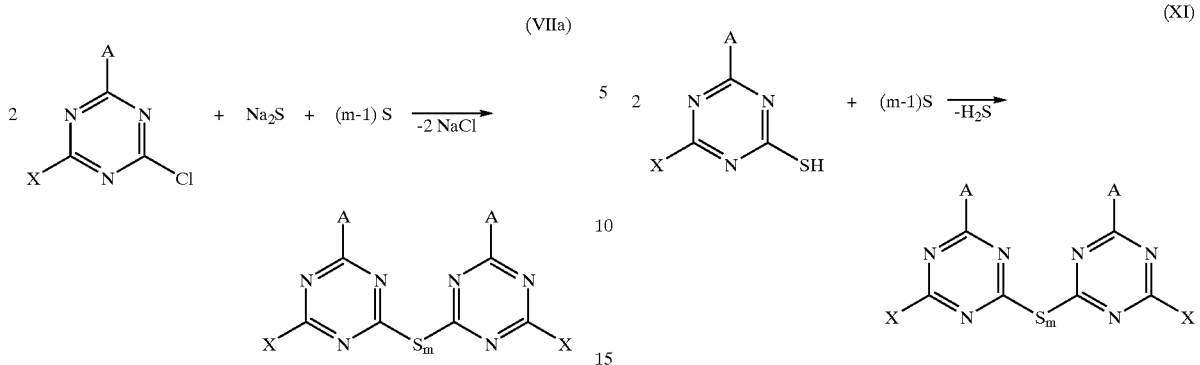

(VIIa)

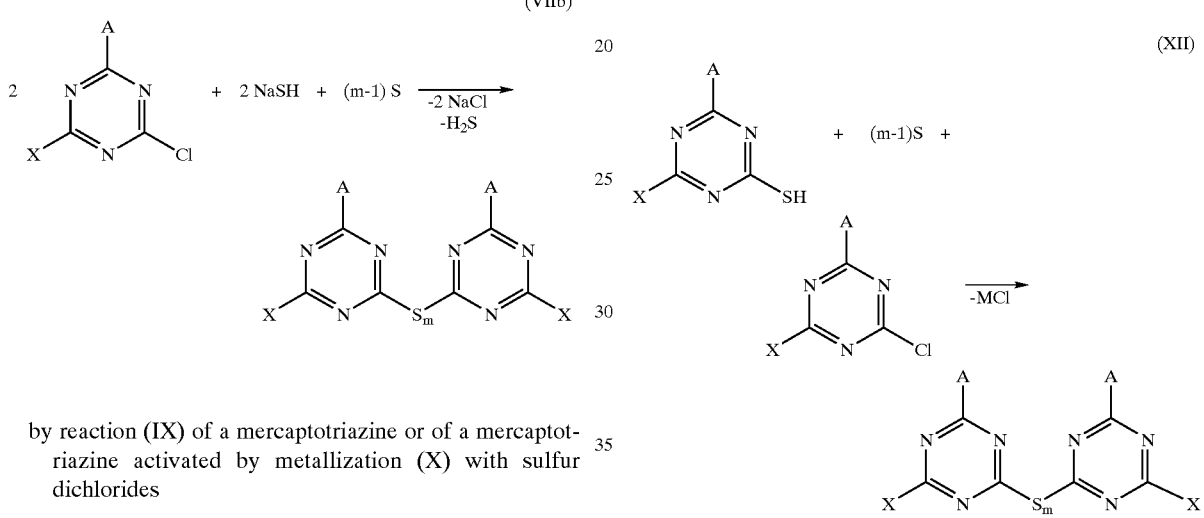

by reaction (IX) of a mercaptotriazine or of a mercaptotriazine activated by metallization (X) with sulfur dichlorides

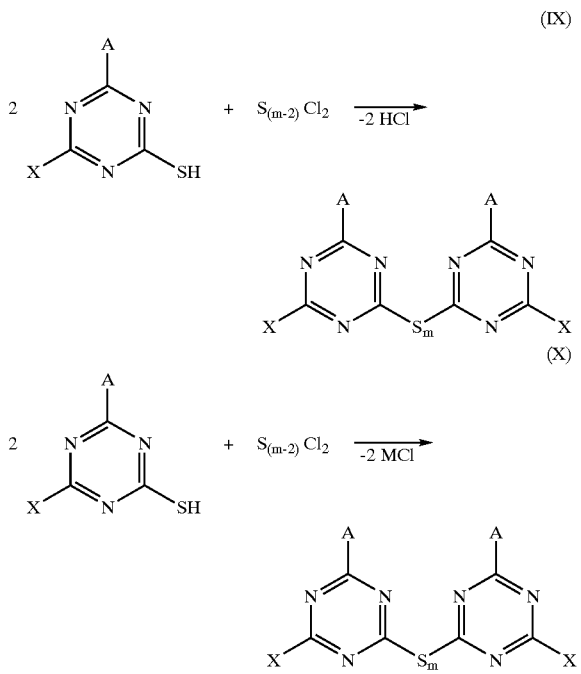

by reaction (XI) of a mercaptotriazine with elemental sulfur at elevated temperature or by reaction (XII) of a mercaptotriazine activated by metallization with sulfur and a chlorine-substituted triazine derivative The sequence of the reaction is unimportant. Preferably, group C can be introduced after group A.

The present invention also provides rubber mixtures which are characterized in that they comprise rubber, filler, preferably precipitated silica, at least one organosilicon compound of the formula (I) and, optionally, further rubber auxiliary substances. Natural rubber and/or synthetic rubbers can be used as the rubber. Preferred synthetic rubbers are described, for example, in W. Hofmann, Kautschuktechnologie [Rubber Technology], Genter Verlag, Stuttgart (1980). The rubbers can be used both by themselves and in combination. Anionically polymerized L-SBR rubbers with a glass transition temperature above −50° C. and mixtures thereof with diene rubbers of high cis content can be employed in particular for the production of motor vehicle tires.

Fillers which can be employed are:
  carbon blacks which are prepared by the flame black, furnace or gas black process and have BET surface areas of 20 to 200 $m^2/g$;
  highly disperse silicas prepared, for example, by precipitations from silicate solutions or by flame hydrolysis of silicon halides, with specific surface areas of 5 to 1000 $m^2/g$, preferably 20 to 400 $m^2/g$ (BET surface area) and with primary particles sizes of 10 to 400 mn, optionally also as mixed oxides with other metal oxides, such as Al, Mg, Ca, Ba, Zn and titanium oxides;
  synthetic silicates, such as aluminium silicate, alkaline earth metal silicates, such as, for example, magnesium silicate or calcium silicate, with BET surface areas of 20 to 400 m²/g and primary particle diameters of 10 to 400 nm;

naturally occurring silicates, such as kaolin and other naturally occurring silicas; or glass fibres and glass fibre products (mats, strands) or glass microbeads.

The rubber mixtures can comprise synthetic rubber and silica as the filler. Preferably, highly disperse silicas prepared by precipitation from silicate solutions, with BET surface areas of 20 to 400 m²/g are employed, in amounts of 10 to 150 parts by wt. based on 100 parts by wt. of rubber. The fillers mentioned can be employed by themselves or as a mixture.

The organosilicon compounds according to the invention can be used either in pure form or in a form absorbed on an inert organic or inorganic support. Preferred support materials can be silica, naturally occurring or synthetic silicates, aluminium oxide or carbon blacks. The organosilicon compounds according to the invention can be used by themselves or in combination with other organosilicon compounds, in particular monofunctional alkylalkoxysilanes.

Rubber auxiliary products which can be used are reaction accelerators, reaction retardants, anti-ageing agents, stabilizers, processing auxiliaries, plasticizers, waxes, metal oxides and activators, such as triethanolamine, polyethylene glycol, hexanetriol, which are known to the rubber industry.

The advantage of the organosilicon compounds according to the invention is that these act as coupling reagents and, with suitable substituents on the triazine ring, also as accelerators or anti-ageing or anti-fatigue agents. The organosilicon compounds according to the invention are furthermore suitable as adhesion promoters for rubber-metal and rubber-fibre compounds, in particular with primary or secondary amino substituents on the triazine ring.

EXAMPLES

Example 1

Preparation of 1,3,5-tris (triethoxysilylpropylmercaptyl)triazine from cyanuric chloride and 3-mercaptopropyltriethoxysilane 62.7 g triethylamine are added to 36.6 g cyanuric chloride at 0° C. in a 1 l three-necked flask with a reflux condenser, internal thermometer and dropping funnel. 143.1 g mercaptopropyltriethoxysilane are added dropwise to this mixture, while cooling. A white precipitate immediately precipitates out. When the addition has ended, the mixture is stirred at 20–25° C. for a further 2 h and then heated under reflux for 5 h. After cooling, the triethylammonium chloride which has precipitated out is separated off by filtration, the filter cake is washed four times with 75 ml toluene each time and the combined filtrates are evaporated in vacuo. After the solid has been separated off again, 155.4 g of a yellow oil are obtained. 1,3,5-Tris(triethoxysilylpropylmercaptyl)triazine is demonstrated by $^1$H-NMR.

Example 2

Preparation of 1,3,5-tris (triethoxysilylpropylmercaptyl)triazine from the trisodium salt of 1,3,5-trimercaptotriazine and 3-chloropropyltriethoxysilane 24.3 g of the trisodium salt of 1,3,5-trimercaptotriazine are suspended in 75 ml ethanol, and 72.2 g chloropropyltriethoxysilane and 0.3 g Aliquat 336 are added. The mixture is kept at 140° C. in an autoclave for 5 h, while stirring. After cooling to room temperature, the sodium chloride formed is filtered off, the precipitate is washed 4 times with 20 ml ethanol each time and the combined filtrates are evaporated in vacuo. A little precipitate which has precipitated out is filtered off again. 75.3 g of a yellow oil are obtained. 1,3,5-Tris(triethoxysilylpropylmercaptyl)triazine is demonstrated by $^1$H-NMR.

Example 3

Preparation of 1-(di(n-butyl)amino)-3-triethoxysilylpropylmercaptyl-5-(1-methoxypropyl) aminotriazine from the sodium salt of 1-(di(n-butyl) amino)-3-mercaptyl-5-(1-methoxypropyl) aminotriazine and 3-chloropropyltriethoxysilane 17.47 g of the sodium salt of 1-(di(n-butyl)amino)-3-mercaptyl-5-(1-methoxypropyl)aminotriazine is dissolved in 75 ml ethanol in a 250 ml three-necked flask with a reflux condenser, internal thermometer and dropping funnel. 12.0 g 3-chloropropyltriethoxysilane are allowed to run into this mixture at room temperature and the mixture is heated under reflux for 3 h. After cooling to room temperature, the sodium chloride precipitate formed is filtered off and the filter cake is washed four times with 20 ml ethanol each time. The combined filtrates are evaporated in vacuo. 21.70 g of a yellow oil are obtained. 1-(Di(n-butyl)amino)-3-triethoxysilylpropylmercaptyl-5-(1-methoxypropyl) aminotriazine is shown by $^1$H-NMR.

Example 4

Preparation of bis(5,5'-(1-dimethylamino-3-triethoxysilylpropylmercaptyltriazine)tetrasulfane from 5-chloro-1-dimethylamino-3-triethoxysilylpropylmercaptyltriazine and disodium tetrasulfide A mixture of 86.6 g 5-chloro-1-dimethylamino-3-triethoxysilylpropylmercaptyltriazine and 20 ml toluene is added dropwise to a solution of 17.4 g sodium tetrasulfide in 50 ml water at 95° C. in the presence of a phase transfer catalyst. The initially red-orange aqueous phase decolourizes rapidly. After a reaction time of 60 min the organic phase is separated off and evaporated in vacuo. 89 g bis(5, 5'-(1-dimethylamino-3-triethoxysilylpropylmercaptyltriazine)tetrasulfane, the identity of which is confirmed by means of $^1$H-NMR spectroscopy, are obtained.

Example 5

Rubber Mixtures

The recipe used for the preparation of the rubber mixtures is given in table 1. The unit phr here means parts by weight per 100 parts of the crude rubber employed.

TABLE 1

| Substance | Comparison example Amount [phr] | Example B1 Amount [phr] | Example B2 Amount [phr] |
| --- | --- | --- | --- |
| 1st stage |  |  |  |
| Buna VSL 5025-1 | 96.0 | 96.0 | 96.0 |
| Buna CB 24 | 30.0 | 30.0 | 30.0 |

TABLE 1-continued

| Substance | Comparison example Amount [phr] | Example B1 Amount [phr] | Example B2 Amount [phr] |
|---|---|---|---|
| Ultrasil 7000 GR | 80.0 | 80.0 | 80.0 |
| ZnO | 3.0 | 3.0 | 3.0 |
| Stearic acid | 2.0 | 2.0 | 2.0 |
| Naftolen ZD | 10.0 | 10.0 | 10.0 |
| Vulkanox 4020 | 1.5 | 1.5 | 1.5 |
| Protector G35P | 1.0 | 1.0 | 1.0 |
| Bis(triethoxysilyl-propyl)disulfane | 5.8 | — | — |
| Silane of the formula (XIII) | — | 5.0 | 6.1 |
| 2nd stage Batch stage 1 | | | |
| 3rd stage Batch stage 2 | | | |
| Vulkacit D | 1.5 | 1.5 | 1.5 |
| Vulkacit CZ | 1.5 | 1.5 | 1.5 |
| Sulfur | 2.1 | 2.1 | 2.1 |

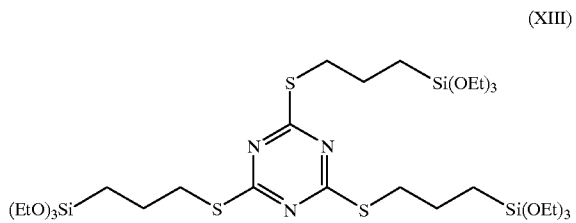

(XIII)

The polymer VSL 5025-1 is an SBR copolymer of Bayer AG polymerized in solution and having a styrene content of 25 wt. % and a 1,2-butadiene content of 50%. The copolymer also comprises 37.5 phr oil.

The polymer Buna CB 24 is a cis-1,4-polybutadiene (neodymium type) from Bayer AG with a cis-1,4 content of 97%, a trans-1,4 content of 2%, a 1,2 content of 1%.

The silica Ultrasil 7000 GR from Degussa AG has a BET surface area of 175 m²/g. The bis(triethoxysilylpropyl) disulfane has a disulfane content of 85%.

Naftolen ZD from Chemetall is used as the aromatic oil; Vulkanox 4020 is PPD from Bayer AG, and Protector G35P is an anti-ozonant wax from HB-Fuller GmbH. Vulkacit D (DPG) and Vulkacit CZ (CBS) are commercial products from Bayer AG.

The rubber mixtures are prepared in three stages in an internal mixer in accordance with the following tabular list (table 2):

TABLE 2

Stage 1

Settings

| Mixing unit | Werner & Pfleiderer E-type |
|---|---|
| Friction | 1:1 |
| Speed | 70 min$^{-1}$ |
| Plunger pressure | 5.5 bar |
| Empty volume | 1.6 L |
| Filling level | 0.55 |
| Flow temp. | 80° C. |

TABLE 2-continued

Mixing operation

| 0 to 1 min | Buna VSL 5025-1 + Buna CB 24 |
|---|---|
| 1 to 3 min | ½ Ultrasil 7000 GR, ZnO, stearic acid, Naftolen ZD, silane |
| 3 to 4 min | ½ Ultrasil 7000 GR, Vulkanox 4020, Protector G35P |
| 4 min | clean |
| 4 to 5 min | mix |
| 5 min | clean |
| 5 to 6 min | mix and deliver |
| Batch temp. | 140–150° C. |
| storage | 24 h at room temperature |

Stage 2

Settings

| Mixing unit | As in stage 1 except: |
|---|---|
| Speed | 80 min$^{-1}$ |
| Filling level | 0.53 |
| Flow temp. | 80° C. |

Mixing operation

| 0 to 2 min | Break up batch stage 1 |
|---|---|
| 2 to 5 min | batch temperature 150° C. maintained by varying the speed deliver |
| 5 min | |
| Batch temp. | 150–155° C. |
| Storage | 4 h at room temperature |

Stage 3

Settings

| Mixing unit | As in stage 1 except: |
|---|---|
| Speed | 40 min$^{-1}$ |
| Filling level | 0.51 |
| Flow temp. | 50° C. |

Mixing operation

| 0 to 2 min | Batch stage 2 + Vulkacit CZ + Vulkacit D + sulfur |
|---|---|
| 2 min | deliver and form a sheet on a laboratory roll mill flow temperature 50° C.) Homogenization: cut in 3* left, 3* right, and fold over and also pass through 8* with a narrow roll nip (1 mm) and 3* with a wide roll nip (3.5 mm) and then draw out a skin |
| Batch temp. | 85–95° C. |

The general process for the preparation of rubber mixtures and vulcanization products thereof is described in "Rubber Technology Handbook", W. Hofmann, Hanser Verlag 1994. The vulcanization time for the test specimens is 30 minutes at 165° C. The rubber testing is carried out in accordance with the test methods described in table 3.

TABLE 3

| Physical testing | Standard/Conditions |
|---|---|
| ML 1 + 4, 100° C. | DIN 53523/3, ISO 667 |
| Vulcameter test, 165° C. | DIN 53529/3, ISO 6502 |
| Tensile test on ring, 23° C. Tensile strength Moduli Elongation at break | DIN 53504, ISO 37 |

TABLE 3-continued

| Physical testing | Standard/Conditions |
|---|---|
| Shore A hardness, 23° C. | DIN 53 505 |
| Viscoelastic properties, 0 and 60° C., 16 Hz, 50 N preliminary force and 25 N amplitude force Complex E* modulus, Loss factor tanδ Ball rebound | DIN 53,513, ISO 2856 |
| DIN abrasion, 10 N force | DIN 53 516 |
| Dispersion | DIN/ISO 11 345 |
| Mooney scorch, 130° C. t5, t 35 | DIN 53523, ISO 667 |

Table 4 shows the rubber data.

TABLE 4

| Mixture | | -1- Comparison example | -2- Example B1 | Example B2 |
|---|---|---|---|---|
| Crude mixture results: | | | | |
| ML 1 + 4 (3rd mixing stage) | [MU] | 61 | 64 | 64 |
| Mooney scorch (135° C.) t5 | [min] | >60 | >60 | >60 |
| t10% at 165° C. | [min] | 2.7 | 1.1 | 1.4 |
| t90% at 165° C. | [min] | 25.2 | 28.7 | 21.5 |
| Dmax-Dmin at 165° C. | [dNm] | 17.3 | 20.5 | 18.5 |
| Vulcanization product results: | | | | |
| Shore A hardness | [SH] | 66 | 67 | 67 |
| Tensile strength | [MPa] | 13.1 | 13.7 | 14.4 |
| Modulus 100% | [MPa] | 1.9 | 1.8 | 1.8 |
| Modulus 300% | [MPa] | 8.9 | 7.8 | 8.2 |
| Modulus 300%/100% | [—] | 4.6 | 4.3 | 4.5 |
| Elongation at break | [%] | 380 | 440 | 440 |
| Breaking energy | [J] | 66.4 | 81.2 | 87.5 |
| Ball rebound 0° C. | [%] | 10.5 | 11.0 | 10.6 |
| Ball rebound 60° C. | [%] | 59.4 | 57.1 | 56.6 |
| DIN abrasion | [mm³] | 87.7 | 101.7 | 100.4 |
| Dyn. extension modulus E' (0° C.) | [MPa] | 20.4 | 21.1 | 24.9 |
| Dyn. extension modulus E' (60° C.) | [MPa] | 7.7 | 7.6 | 8.1 |
| Dyn. extension modulus E" (0° C.) | [MPa] | 10.6 | 11.1 | 13.2 |
| Dyn. extension modulus E" (60° C.) | [MPa] | 1.1 | 1.1 | 1.2 |
| Loss factor tanδ (0° C.) | [—] | 0.518 | 0.529 | 0.531 |
| Loss factor tanδ (60° C.) | [—] | 0.137 | 0.151 | 0.152 |
| Dispersion | [—] | 8 | 7 | 7 |

The examples show that a filler-rubber binding has taken place. In an equimolar dosage (6.1 ph), the static and also the dynamic data demonstrate a polymer binding.

Example 6

Preparation of 1,3-diethoxy-5-triethoxysilylpropylmercaptyltriazine from 1,3-diethoxy-5-chloropropyltriethoxysilane 80.0 g (0.4 mol) 1,3-diethoxy-5-triethoxysilylpropylmercaptyltriazine in 200 ml ethanol are added to a solution consisting of 9.1 g (0.4 mol) sodium in 300 ml ethanol at 50° C. After 20 minutes at 50° C., 95.7 g (0.4 mol) chloropropyltriethoxysilane are added dropwise. The mixture is then stirred at 78° C. for 6 h. After cooling to room temperature, the precipitate which has precipitated out is filtered off and the solvent (ethanol) is removed on a rotary evaporator. 121.7 g 1,3-diethoxy-5-triethoxysilylpropylmercaptyltriazine, the identity of which is confirmed by means of $^1$H-NMR spectroscopy, are obtained.

Example 7

Rubber Mixtures

The recipe used for the preparation of the rubber mixtures is given in table 5. The silane of example B3 is employed in an equimolar amount and the silane of example B4 is employed in an equal weight with respect to the silane of the reference mixture.

TABLE 5

| Substance | Comparison example Amount [phr] | Example B3 Amount [phr] | Example B4 Amount [phr] |
|---|---|---|---|
| 1st stage | | | |
| Buna VSL 5025-1 | 96.0 | 96.0 | 96.0 |
| Buna CB 24 | 30.0 | 30.0 | 30.0 |
| Ultrasil 7000 GR | 80.0 | 80.0 | 80.0 |
| ZnO | 3.0 | 3.0 | 3.0 |
| Stearic acid | 2.0 | 2.0 | 2.0 |
| Naftolen ZD | 10.0 | 10.0 | 10.0 |
| Vulkanox 4020 | 1.5 | 1.5 | 1.5 |
| Protector G35P | 1.0 | 1.0 | 1.0 |
| Bis(triethoxysilyl-propyl)tetra-sulfane(Si69) | 6.4 | — | — |
| Silane according to example 6 | — | 9.74 | 6.4 |
| 2nd stage | | | |
| Batch stage 1 | | | |
| 3rd stage | | | |

TABLE 5-continued

| Substance | Comparison example Amount [phr] | Example B3 Amount [phr] | Example B4 Amount [phr] |
|---|---|---|---|
| Batch stage 2 | | | |
| Vulkacit D | 1.5 | 1.5 | 1.5 |
| Vulkacit CZ | 1.5 | 1.5 | 1.5 |
| Sulfur | 1.5 | 2.2 | 2.2 |

The rubber mixtures are prepared in three stages, as in example 5, table 2. The vulcanization time for the test specimens is 30 minutes for the comparison example and example B3 and for example B4 45 minutes at 165° C. The rubber testing is carried out in accordance with the test methods given in example 5, table 3.

Table 6 show the rubber data.

TABLE 6

| Mixture | | Comparison example -Si 69 ref- | Example B3 -1- equimolar | Example B4 -2- equal wt. |
|---|---|---|---|---|
| Crude mixture results: | | | | |
| ML(1 + 4) at 100° C., 3rd stage | [MU] | 64 | 52 | 58 |
| Scorch time, t5 (135 ° C.) | [mm] | 38.9 | 57.5 | 56.5 |
| Scorch time, t35 (135 ° C.) | [mm] | 54.3 | >60 | >60 |
| Dmax-Dmin at 165° C. | [dNm] | 16.9 | 16.4 | 20.7 |
| t10% at 165° C. | [mm] | 1.8 | 4.9 | 3.6 |
| t90% at 165° C. | [mm] | 19.5 | 28.2 | 50.0 |
| Vulcanization product results: | | | | |
| Tensile strength | [MPa] | 11.0 | 10.6 | 12.3 |
| Modulus 100% | [MPa] | 1.7 | 1.4 | 1.6 |
| Modulus 300% | [MPa] | 9.1 | 6.1 | 6.9 |
| Modulus 300%/100% | [—] | 5.2 | 4.3 | 4.3 |
| Elongation at break | [%] | 340 | 440 | 450 |
| Breaking energy | [J] | 46.7 | 63.8 | 75.8 |
| Shore A hardness | [SH] | 64 | 63 | 66 |
| Ball rebound, 23° C. | [%] | 32.4 | 22.2 | 25.0 |
| Storage modulus E', 0° C. | [MPa] | 16.6 | 27.5 | 23.8 |
| Storage modulus E', 60° C. | [MPa] | 7.1 | 6.6 | 7.4 |
| Loss modulus E", 0° C. | [MPa] | 8.4 | 16.4 | 13.4 |
| Loss modulus E", 60° C. | [MPa] | 1.0 | 1.2 | 1.3 |
| Loss factor tanδ (0° C.) | [—] | 0.508 | 0.596 | 0.563 |
| Loss factor tanδ (60° C.) | [—] | 0.135 | 0.182 | 0.172 |
| Dispersion | [—] | 9 | 9 | 9 |

Examples B3 and B4 (silane according to example 6) show a rubber-filler coupling action, longer scorch time and lower viscosity compared with the comparison example.

Example 8

Preparation of bis-[2-diethylamino-4-(3-triethoxysilylpropyl)mercapto-s-triazin-6-yl]-polysulfide (XIV)

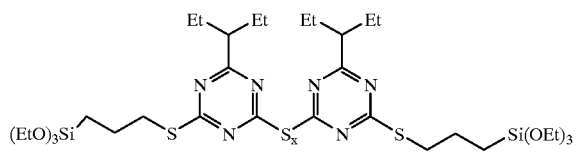

(XIV)

116.8 g of mercaptopropyltriethoxysilane are added dropwise at 10° C. to a solution of 108.4 g of 2-diethylamino-4,6-dichloro-s-triazine and 58.0 g of triethylamine in 500 ml of toluene. The reaction mixture is then stirred for 1 h at room temperature. The precipitate which has precipitated out is filtered off and the solvent (toluene) is removed on a rotary evaporator. 213.6 g of liquid product are obtained, which are added dropwise at room temperature to a suspension of 45.7 g of sodium polysulfide ($Na_2S_{3.8}$) in 500 ml of ethanol, and the whole is then stirred for 2 h at 80° C. under reflux. After cooling to room temperature the precipitate is filtered off and the filtrate is freed from ethanol on a rotary evaporator. 185.8 g of a waxy solid are obtained, whose identity is confirmed by means of $^1H$ spectroscopy and $^{13}C$ NMR spectroscopy. The mean sulfur chain length x is 3.8.

Example 9

Rubber Mixtures

The recipe used for the preparation of the rubber mixtures is given in table 7.

TABLE 7

| Substance | Comparison Example I Amount [phr] | Example B5 Amount [phr] |
|---|---|---|
| 1st stage | | |
| Buna VSL 5025-1 | 96.0 | 96.0 |
| Buna CB 24 | 30.0 | 30.0 |
| Ultrasil 7000 GR | 80.0 | 80.0 |
| ZnO | 3.0 | 3.0 |
| Stearic acid | 2.0 | 2.0 |
| Naftolen ZD | 10.0 | 10.0 |
| Vulkanox 4020 | 1.5 | 1.5 |
| Protector G35P | 1.0 | 1.0 |
| bis(triethoxysilylpropyl)-tetrasulfane(Si69) | 6.4 | — |
| Silane according to example 8 | | 10.8 |
| 2nd stage | | |
| Batch stage 1 | | |
| 3rd stage | | |
| Batch stage 2 | | |
| Vulkacit D | 1.5 | 1.5 |
| Vulikacit CZ | 1.5 | 1.5 |
| Sulfur | 1.5 | 1.5 |

The silane according to example 8 is metered in example B5 in an equimolar amount, referred to the triethoxysilyl function, to the comparison example I with Si 69, corresponding to an amount of 10.8 phr. 1.5 phr sulfur is added in all mixtures and worked up according to the mixing instructions given in example 5, table 2. The vulcanisation time for the test specimens is 20 minutes at 165° C. The rubber testing is carried out in accordance with the test methods given in example 5, table 3.

Table 8 shows the rubber data.

TABLE 8

| Mixture | | Comparison Example I -Si 69 Ref- | Example B5 Equimolar |
|---|---|---|---|
| Crude mixture results | | | |
| ML(1 + 4) at 100° C. 3rd stage | [ME] | 67 | 66 |
| Dmax-Dmin at 165° C. | [dNm] | 16.7 | 21.1 |
| t10% | [min] | 1.6 | 1.0 |
| t90% | [min] | 7.4 | 13.3 |
| Vulcanisation results | | | |
| Tensile strength | [MPa] | 11.4 | 10.5 |
| Modulus 100% | [MPa] | 1.7 | 3.5 |
| Modulus 300% | [MPa] | 8.8 | — |
| Modulus 300%/100% | [—] | 5.2 | — |
| Elongation at break | [%] | 350 | 210 |
| Breaking energy | [J] | 50 | 30 |
| Shore A hardness | [SH] | 62 | 73 |
| DIN abrasion | [mm$^3$] | 79 | 66 |
| Ball rebound, 23° C. | [%] | 33.6 | 33.3 |
| Complex modulus E*, 0° C. | [MPa] | 17.2 | 27.7 |
| Complex modulus E*, 60° C. | [MPa] | 7.5 | — |
| Loss factor tan δ 0° C. | [—] | 0.484 | 0.440 |
| Loss factor tan δ 60° C. | [—] | 0.121 | — |
| Phillips dispersion | [—] | 7 | 7 |

As can be seen from the data in table 8, the equimolar addition of the silane according to the invention (example B5) leads to a high crosslinking density, which is reflected in a very high $D_{max}$–$D_{min}$ value, a high hardness, high moduli, and short elongation at break. This raised crosslinking density is also attributed to the sulfur donor function of the polysulfane function, in addition to the high coupling yield.

Example 10

Rubber Mixtures

The recipe used for the preparation of the rubber mixtures is given in table 9.

TABLE 9

| Substance | Comparison Example II Amount [phr] | Example B6 Amount [phr] |
|---|---|---|
| 1st stage | | |
| Buna VSL 5025-1 | 96.0 | 96.0 |
| Buna CB 24 | 30.0 | 30.0 |
| Ultrasil 7000 GR | 80.0 | 80.0 |
| ZnO | 3.0 | 3.0 |
| Stearic acid | 2.0 | 2.0 |
| Naftolen ZD | 10.0 | 10.0 |
| Vulkanox 4020 | 1.5 | 1.5 |
| Protector G35P | 1.0 | 1.0 |
| bis(triethoxysilylpropyl)-tetra-sulfane(Si69) | 6.4 | — |
| Silane according to example 8 | — | 6.4 |
| Octyltriethoxysilane (Si 208) | | 2.0 |
| 2nd stage | | |
| Batch stage 1 | | |
| 3rd stage | | |

TABLE 9-continued

| Substance | Comparison Example II Amount [phr] | Example B6 Amount [phr] |
|---|---|---|
| Batch stage 2 | | |
| Vulkacit D | 1.5 | 1.5 |
| Vulkacit CZ | 1.5 | 1.5 |
| Sulfur | 1.5 | 1.5 |

In example B6 the silane from example 8 is added in the same amount by weight (6.4 phr) as in comparison example II. In order to compensate for the lower hydrophobing of this silane when added in the same amount by weight, corresponding to a smaller amount of substance, 2 phr of the monofunctional alkylsilane octyltriethoxysilane (Si 208) are additionally added. A reaction of Si 208 with the rubber is avoided.

In all mixtures 1.5 phr of sulfur is added and worked up according to the mixing instructions in example 5, table 2. The vulcanisation time for the test specimens is 20 minutes at 165° C. The rubber testing is carried out in accordance with the test methods given in example 5, table 3.

Table 10 shows the rubber data.

TABLE 10

| Mixture | | Comparison Example II -Si 69 Ref- | Example B6 equal weight |
|---|---|---|---|
| Crude mixture results | | | |
| ML(1 + 4) at 100° C. 3rd stage | [ME] | 65 | 60 |
| Dmax-Dmin at 165° C. | [dNm] | 16.0 | 15.6 |
| t10% | [min] | 1.8 | 2.5 |
| t90% | [min] | 17.7 | 21.9 |
| Vulcanisation results | | | |
| Tensile strength | [MPa] | 11.6 | 11.2 |
| Modulus 100% | [MPa] | 1.8 | 1.8 |
| Modulus 300% | [MPa] | 9.1 | 9.8 |
| Modulus 300%/100% | [—] | 5.1 | 5.4 |
| Elongation at break | [%] | 350 | 330 |
| Breaking energy | [J] | 53 | 46 |
| Shore A hardness | [SH] | 63 | 62 |
| DIN abrasion | [mm$^3$] | 81 | 84 |
| Ball rebound, 23° C. | [%] | 33.9 | 31.8 |
| Complex modulus E*, 0° C. | [MPa] | 12.5 | 13.0 |
| Complex modulus E*, 60° C. | [MPa] | 6.6 | 6.6 |
| Loss factor tan δ 0° C. | [—] | 0.459 | 0.472 |
| Loss factor tan δ 60° C. | [—] | 0.129 | 0.113 |
| Phillips dispersion | [—] | 8 | 7 |

In example B6 the compound is added in an equal amount by weight and the higher viscosity to be expected due to the decreased use of silane is compensated by metering in the hydrophobing aid octyltriethoxysilane Si 208. The results of example B6 show an advantageously low viscosity, high moduli, a high reinforcement ratio 300%/100%, as well as an advantageously low tan tan δ (60° C.) value, which point to a very good filler-polymer binding effect.

What is claimed is:

1. An organosilicon compound of the general formula I,

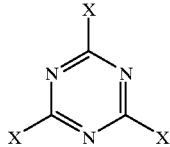
(I)

characterized in that the substituents X are identical or different and X is one of the following groups A, B, or C:

$A = Y-R^1-S_n-$, where

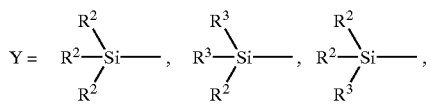

where:
- $R^2$ = alkoxy radical having 1 to 4 C atoms,
- $R^3$ = alkyl radical having 1 to 8 C atoms,
- $R^1$ = linear or branched hydrocarbon having 1 to 10 C atoms,
- n = 1 to 8 or mixtures thereof, $B = -OR^4$, $-NR^5R^6$, $-SR^7$, $-SCN$, or $-CO-R^8$ where
- $R^4, R^5, R^6, R^7$ = H, branched or unbranched alkyl radical having 1 to 10 C atoms or substituted or unsubstituted aromatic radical having 6 to 30 C atoms, which is optionally interrupted by N, S, or O atoms,
- $R^8$ = linear or branched alkyl radical having 1 to 20 C atoms, $C = (S_m)/2$, where m = 1 to 8, or mixtures thereof with the proviso that group C bridges two triazine units; at least one group A is present in the molecule; and the combination of a group A together with two mercapto groups or a mercapto group and an amino group $-NR^5R^6$ is excluded.

2. A process for the preparation of organosilicon compounds according to claim 1, wherein:

(i) reaction (II) of a chlorine-substituted triazine base structure with mercaptosilanes of the corresponding structure in the presence of an acid-trapping agent (II)

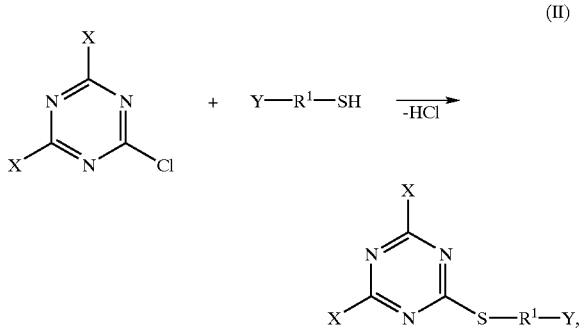

(ii) reaction (III) of a metallized mercaptotriazine with a chloroalkylsilane wherein X=A and, for n>1, in the presence of elemental sulfur, (III)

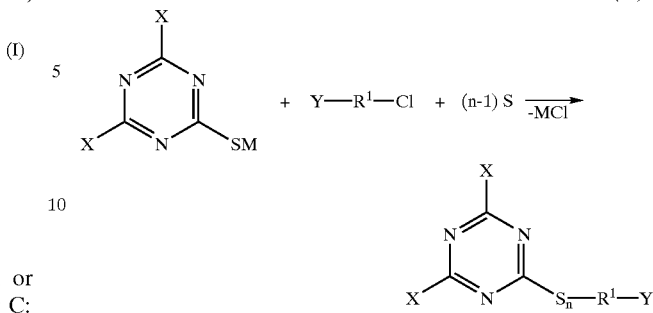

where M=metal (iii) reaction (IV) of a chlorine-substituted triazine skeleton with alcohols, amines, or mercaptans in the presence of an acid-trapping agent (IV)

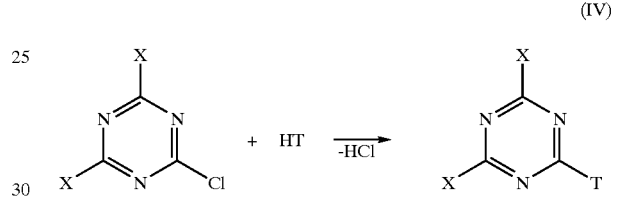

where T = $-OR^4$, $-NR^5R^6$, or $-SR^7$, (iv) reaction (V) of a chlorine-substituted triazine skeleton with metallized mercaptotriazine alcohols, amines, or mercaptans (V)

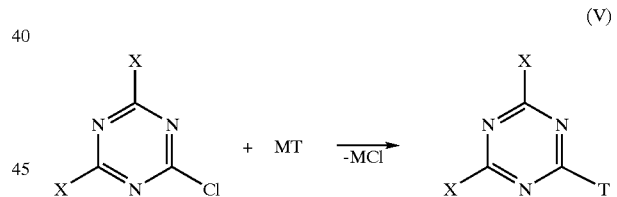

where M=metal, (v) alkylation (VIa) or (VIb) of amino- and mercaptyl-substituted triazines with highly alkylating substances (VIa)

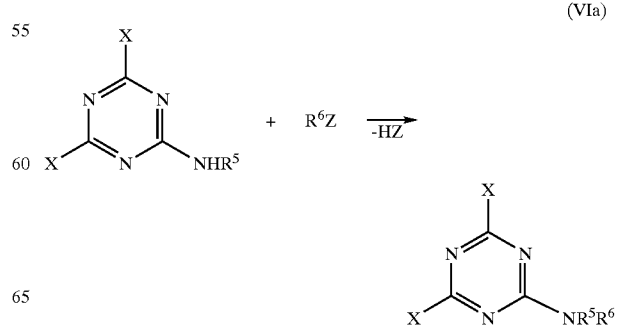

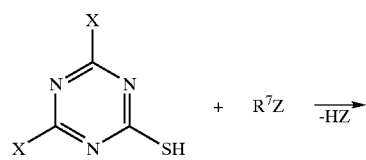
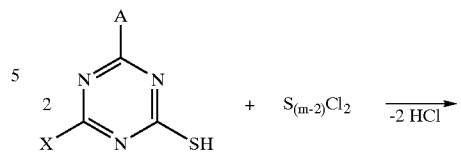

(vi) reaction (VII) of a chlorine-substituted triazine skeleton with a sodium polysulfide (VII)

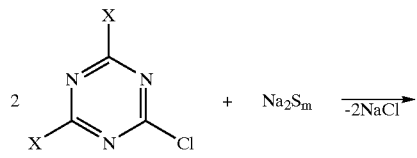

or a mixture of sodium sulfide (VIIIa) or sodium hydrogen sulfide (VIIIb) and sulfur (VIIIa)

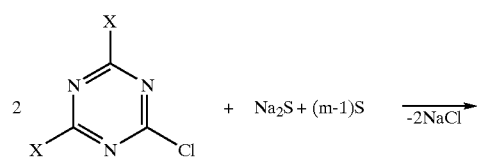

(VIIIb)

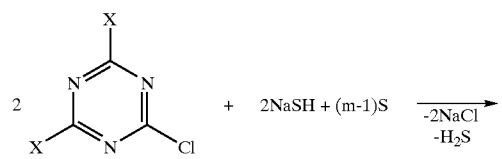

(vii) reaction (IX) of a mercaptotriazine, or of a mercaptotriazine activated by metallization (X), with sulfur dichlorides (IX)

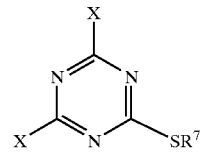

(X)

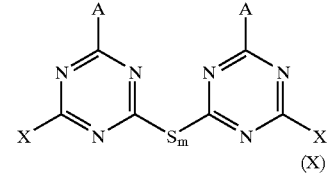

where M=metal, (viii) reaction (XI) of a mercaptotriazine with elemental sulfur at elevated temperature (XI)

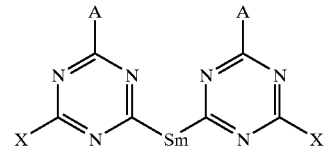

or, (ix) reaction (XII) of a mercaptotriazine activated by metallization with sulfur and a chlorine-substituted triazine derivative (XII)

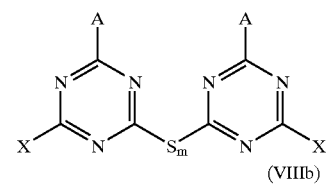
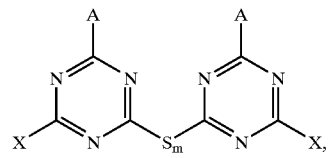
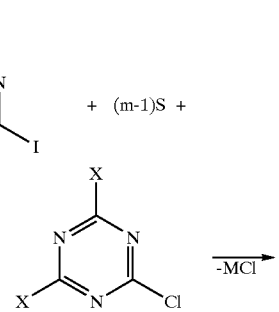

-continued
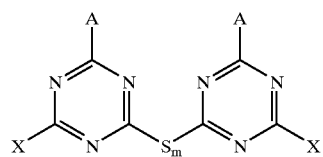
3. A rubber mixture comprising the organosilicon compound of formula (I) according to claim 1.
4. A rubber mixture comprising: rubber; filler; and at least one organosilicon compound of formula (I) according to claim 1.
5. The rubber mixture of claim 4, further comprising rubber auxiliary substances.
* * * * *